(12) United States Patent
Black et al.

(10) Patent No.: US 8,463,552 B1
(45) Date of Patent: Jun. 11, 2013

(54) METHODS FOR MEDICINAL DOSAGE DETERMINATION AND DIAGNOSIS

(76) Inventors: Kevin J. Black, Crestwood, MO (US); Jonathan M. Koller, Crestwood, MO (US)

( * ) Notice: Subject to any disclaimer, the term of this patent is extended or adjusted under 35 U.S.C. 154(b) by 1031 days.

(21) Appl. No.: 11/583,896

(22) Filed: Oct. 18, 2006

Related U.S. Application Data

(60) Provisional application No. 60/728,034, filed on Oct. 18, 2005.

(51) Int. Cl.
| | |
|---|---|
| G06F 19/10 | (2011.01) |
| G01N 24/00 | (2006.01) |
| B01D 59/44 | (2006.01) |

(52) U.S. Cl.
USPC .............................. 702/19; 436/173; 250/281

(58) Field of Classification Search
None
See application file for complete search history.

(56) References Cited

U.S. PATENT DOCUMENTS

| | | | |
|---|---|---|---|
| 6,321,105 B1 | 11/2001 | Jenkins et al. | |
| 7,043,415 B1 | 5/2006 | Dunlavey et al. | |
| 2003/0012731 A1* | 1/2003 | Suddarth et al. ............. | 424/1.49 |
| 2006/0089592 A1 | 4/2006 | Kadhiresan et al. | |

FOREIGN PATENT DOCUMENTS

| | | |
|---|---|---|
| EP | 960105625 | 10/1996 |

OTHER PUBLICATIONS

Zuideveld et al. (European Journal of Pharmacology 445 (2002) 43-54).*
Meyer et al. (J Neuroimaging 2001;11:30-39).*
Jonsson et al. (Computer Methods and Programs in Biomedicine, vol. 58, (1999), p. 51-64).*
Furey et al. (Pharmacology Biochemistry and Behavior, vol. 66, No. 3, pp. 475-481, 2000).*
Wiesenberger et al. (IEEE Transactions on Nuclear Science, vol. 50, No. 1, Feb. 2003).*
Leslie et al. (TiPS—Aug. 2000 (vol. 21), p. 314-318).*
Stevenson et al. (Journal of Clinical Oncology, vol. 21, No. 23 Dec. 1, 2003: pp. 4428-4438).*
Farnec et al. (Computers and Biomedical Research, vol. 33, p. 315-329, 2000).*
Cohen et al. (Journal of Magnetic Resonance Imaging, vol. 10, p. 33-40, 1999).*
Sonami et al. (Drug Metabolism and Disposition, vol. 19, No. 3, p. 655-660).*
Black et al. Dopamine D1 agonist activates temporal lobe structures in primates. J Neurophysiol 84: 549-557, 2000.
Bloom et al. Determination of drug-induced changes in functional MRI signal using a pharmacokinetic model. Hum Brain Mapp 1999; (8):235-244.
Contin et al. Longitudinal monitoring of the levodopa concentration-effect relationship in Parkinson's disease. Neurology. Jul. 1994;44(7):1287-92.
Holford and Sheiner. Kinetics of Pharmacologic Response. Pharmacol. Ther. 16: 143-166, 1982.
Stein et al. Functional MRI in pharmacology. In: Moonen CTW, Bandettini PA, editors. Functional MRI, New York: Springer-Verlag, 1999: 525-538.
Trugman and Wooten. The effects of L-DOPA on regional cerebral glucose utilization . . . Brain Research 379: 264-274, 1986.
Wise et al. Combining fMRI with a pharmacokinetic model . . . Neuroimage 16:999-1014, 2002.
Lalonde et al., Propranolol pharmacodynamic modeling using unbound and total concentrations in healthy volunteers. Journal of Pharmacokinetics and Biopharmaceutics, 15(6):569-581, (1987).
Contin et al., A levodopa kinetic-dynamic study of the rate of progression in Parkinson's disease J. Neurol. 2003, 250:1475-1481 Neurology 51:1075-1080 (1998).

* cited by examiner

*Primary Examiner* — Lori A Clow
(74) *Attorney, Agent, or Firm* — Randolph Bretton

(57) ABSTRACT

The present invention is directed to systems and methods for diagnosing tissue abnormality or diseases, determining effective drug dosages, and monitoring therapeutic drug treatments. The methods and systems described utilize tissue imaging in situ and computer modeling.

17 Claims, 14 Drawing Sheets

Overview of PK-PD model

The pharmacokinetic (PK) model describes the expected changes in blood concentration of drug over time, based on the timing and magnitude of doses, and specific drug properties.

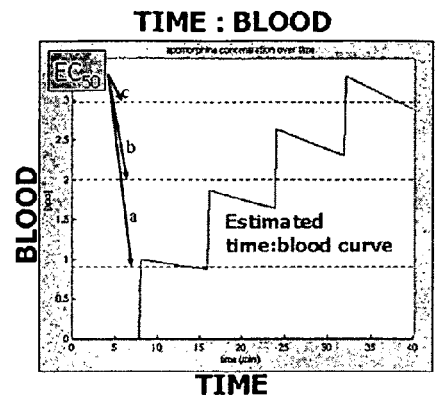

TIME : BLOOD

The pharmacodynamic (PD) model describes the expected tissue responses to a given blood concentration of drug, based on the properties of the tissue effect site, e.g. $EC_{50}$.

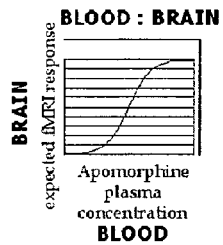

BLOOD : BRAIN

The PK-PD model combines the PK and PD models to describe the expected tissue response over time during the experiment, based on the timing and dose(s) of drug. The top and bottom figures show the different effects of three different $EC_{50}$ values, a, b, and c.

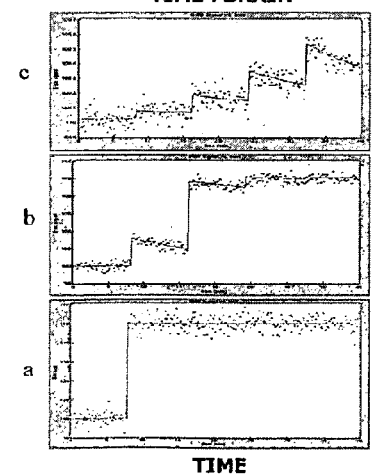

TIME : BRAIN

Figure 2

% voxels "in range" of input ("correct") EC$_{50}$

Example of EC$_{50}$ Image

METHODS FOR MEDICINAL DOSAGE DETERMINATION AND DIAGNOSIS

CROSS-REFERENCE TO RELATED APPLICATIONS

This application claims the benefit of provisional patent application Ser. No. 60/728,034, filed 2005 Oct. 18 by the present inventor.

STATEMENT AS TO RIGHTS TO INVENTIONS MADE UNDER FEDERALLY SPONSORED RESEARCH AND DEVELOPMENT

This invention was made with government support under grant number ROI NS44598 awarded by the National Institutes of Health (NIH). The government has certain rights in the invention.

SEQUENCE LISTING OR PROGRAM

A working model of the computer program described below is attached as Appendix I on a compact disk in duplicate.

FIELD OF THE INVENTION

The present invention is directed to systems and methods for diagnosing tissue diseases, determining effective drug dosages, and monitoring therapeutic drug treatments. The methods and systems described utilize tissue imaging in situ and computer modeling.

BACKGROUND OF THE INVENTION

A large number of psychiatric (i.e. schizophrenia), neurological (i.e. Parkinson's disease), and neurodegenerative (i.e. Huntington's chorea) pathologies involve changes of mental states or conditions based upon changes in neurotransmitter and receptor balances. Detection of such changes may allow for diagnosis well ahead of manifestation of severe clinical symptoms, and knowledge of the nature and the extent of such changes is of paramount importance for the determination of therapy. For instance, in Parkinson's disease the chronic use of L-DOPA therapy leads to a progressive diminution in its efficacy. Thus, one would like to be able to monitor the progression of the disease more closely to effect possible changes in dosing. Similar problems present for many of the currently used dopaminergic ligands in schizophrenia. Determination of the effects of these therapies upon the brain is very difficult at the present time.

The brain provides especially illustrative examples because of various difficulties in accessing the tissue directly during life. In a broader sense, though, many biological questions reduce to "what is the sensitivity of this tissue, or this subject, to a given drug or to other manipulation of a given receptor?"

Some existing methods allow identification of a region of tissue that is especially sensitive to a given pharmacological agent ("mapping"), but do not characterize that response across a range of doses or quantify the sensitivity. This has uses but usually fails for comparisons across long stretches of time or between subject groups.

Two methodologies have been widely used for the determination of changes in neurotransmitter and receptor dynamics in vivo. These two techniques (Positron Emission Tomography and Single Photon Emission Computed Tomography, PET and SPECT) involve the use of radioactivity. Positron Emission Tomography is a very versatile technique which has been used successfully for the mapping and sometimes quantification of Cerebral Blood Flow (CBF), cerebral glucose metabolism (using [$^{18}$F]fluorodeoxyglucose, FDG) or receptor activity (using radioactive pharmacological ligands), while SPECT has until recently been more limited to the detection of nonspecific processes. Unfortunately, both techniques suffer from severe limitations in spatial and temporal resolution, and cannot generally be proposed for repeated applications. Measuring receptor sensitivity quantitatively with PET or SPECT often requires invasive steps such as arterial catheterization. Moreover, PET is characterized by limited availability and high costs, which are partly due to the short half-life of many of the cyclotron-produced radiopharmaceuticals which have to be administered.

A number of existing strategies allow quantification of pharmacological sensitivity in vivo. Traditionally this is done by measuring a biological signal after repeated experiments, each performed at a specific drug dosage, across a wide dose range. The resulting data can be plotted to show a dose-response curve (see FIG. 1). Signals can be quite varied and include clinical information such as blood pressure or subjective emotional state, endocrine responses, measurement of chemicals in tissues or body fluids, volume of an organ, cell number or shape, staining and microscopic examination, or measurement of electrical signals such as electrocardiogram (EKG) or single-neuron electrical recordings.

The area of pharmacology that describes and interprets such information is called pharmacodynamics. Traditionally, data from dose-response curves are fit to a mathematical model of drug-receptor interactions. These pharmacodynamic (PD) models allow characterization of the dose-response curve's shape, and position along the dose axis, by a small number of model parameters. Common models used to describe drug-receptor interactions return parameters such as the $B_{max}$ and $K_D$, often used in tracer kinetic studies, or the $E_{max}$ and $EC_{50}$ or $ED_{50}$, more commonly reported in clinical studies. The parameter $E_{max}$ refers to the maximum possible magnitude of a measured effect even at high doses of drug. The concentration of drug in blood or another body fluid that produces an effect half the magnitude of $E_{max}$ is denoted $EC_{50}$. Instead of blood concentration one can characterize the administered dose of drug similarly; a dose of size $ED_{50}$ produces an effect of magnitude $E_{max}/2$.

All these solutions to calculating quantitative pharmacodynamic information are limited in important ways. These include (a) spatial limitations (such as with needle electrophysiological recordings, microdialysis, or measurements of systemic, e.g. clinical or endocrine, responses; (b) limitations to interpretation at one cellular level, e.g. receptor quantification by PET does not provide a measurement of the sensitivity of the whole complex of receptor and postsynaptic cell(s); and (c) limited pools of subjects, e.g. with autopsy, biopsy, PET, microdialysis, or intrasurgical recordings. Further, PET or SPECT measurements of specific receptors can proceed only after extensive testing of each specific radioligands, including tests of safety, drug distribution including penetration of the organ of interest, radiodosimetry, displaceability, and pharmacological specificity.

An alternative approach has been called pharmacological challenge imaging. In this approach a receptor-effector system is manipulated by administration to the organism of a specific pharmaceutical agent, such as a synthetic agonist at a receptor for an endogenous transmitter or hormone. Additionally, an imaging device, records a response of tissue to this agent. Generally in this case the response, such as glucose or oxygen metabolism, or blood flow, is a general reflection of tissue activity and can also be observed in response to varied other physiological stimuli (such as sensory stimulation, mental work, or physical exercise). Pharmacological challenge imaging has several potential specific advantages: the entire system of receptor and effector mechanisms is probed simultaneously, responses can be measured in numerous locations simultaneously (e.g., across the entire brain), and responses can be seen in numerous regions all of which may be affected by receptor stimulation in the whole organism.

Pharmacologic challenge imaging began with ex vivo rodent studies with autoradiographic studies of local blood flow or metabolism in tissue slices. In the past several decades PET and SPECT have also been used to observe changes in humans and other animals. However, only rarely have quantitative measures been used or a wide range of dosages administered so that one could adequately characterize the dose-response curve to the drug.

More recently, functional magnetic resonance imagine (fMRI) has been used as the imaging method in pharmacological challenge imaging. This application has been dubbed pharmacological Magnetic Resonance Imaging (phMRI). The most common fMRI technique is sensitive to changes in blood oxygen level (Blood Oxygen Level Dependent signal, BOLD). Unfortunately most BOLD-sensitive fMRI is non-quantitative. This implies that responses to drug cannot be determined over a wide range of drug doses. Additionally, quantitative comparisons of drug response over time or between groups in an experiment are largely impossible. The situation is somewhat analogous to measuring distance with a stretchable ruler—it may be useful over short periods of time or in certain clever experimental designs, but one would view with suspicion an apparent difference obtained by measurements from the stretchable ruler taken in two different settings.

Other investigators have sought to circumvent the "stretchable ruler" problem of BOLD-sensitive fMRI by adding additional experimental data. Some groups have used what could be called a pure pharmacokinetic (PK) approach. In this approach, blood levels of drug after a single dose of drug are computed repeatedly over time from a subject or from a group of subjects. The resulting time-concentration curves are used to constrain a search for imaging signals that correspond in time to the expected blood concentrations of the dose of drug. The general plan is to observe changes that occur rapidly in comparison to the more gradual artifactual changes in the nonquantitative signal: by analogy, to measure quickly, before the ruler stretches too much. One serious problem with this method is that it assumes that tissue response is a linear function of drug when in fact two low doses may have indistinguishable or negligible effect and two higher doses may each have maximal effect (FIG. 1). Another problem with this method is that only drugs with rapid onset and rapid removal from the system are suitable. While such drugs exist, e.g. injected nicotine or inhaled cocaine, the reality is that many prescription drugs of interest are selected especially not to have these characteristics. Patients prefer to take only one dose of drug a day, so slow drug elimination is often preferred. Since many side effects are concentration-related, slower absorption and consequently lower peak concentrations are also desired.

Another attempt to circumvent limitations of BOLD fMRI for pharmacological imaging involves what might be called pure pharmacodynamic phMRI. In this method a clinical parameter, such as pain relief by an opiate or a feeling of "high" induced by cocaine, is measured repeatedly over time either in the scanner or during a separate experimental session. The resulting time-response curve is used to constrain a search for imaging signals that correspond in time to the expected clinical effect of the drug. Safety or ethical issues aside, this approach suffers from specific problems including (a) the imaging signal observed cannot easily be interpreted as being a direct effect of drug, rather than an indirect effect of pain relief or feeling "high"; (b) only drugs with an easily detectable clinical effect can be used; and (c) studies of a medicament used for a specific disease will usually require studies only in patients, rather than in control groups, since the control subjects have by definition normal function not expected to improve detectably with administration of drug.

Newer imaging methods may overcome some of the disadvantages of BOLD-sensitive fMRI for pharmacological challenge imaging. Arterial spin labeling (ASL) is one such method that promises to provide more quantitative measures. Images taken after administration of MRI signal enhancing agents ("contrast") can be made quantitative under some circumstances. These methods have their own disadvantages including relatively poor temporal sensitivity or the need to administer the contrast agent with potential side effects.

However, even if the specific disadvantages of existing imaging methods for pharmacological challenge imaging are overcome, they do not generate quantitative pharmacodynamic parameters in current implementations. In fact, in order to generate such quantitative data, all current pharmacological activation imaging approaches require repeated experiments, each after a different dose of a drug of interest, to generate accurate dose-response curves or otherwise to estimate quantitative pharmacodynamic parameters such as EC50. These repeated experiments must also include experiments done at relatively high doses of the challenge drug (e.g., those that produce at least 90% of the maximal possible signal, or doses that can be many times higher than the dose that produces 50% of the maximal possible signal).

To summarize, the prior art is characterized by a state in which quantitative measures of pharmacodynamic parameters require one or more of the following undesirable characteristics: (a) invasive measurements; (b) many measurement (e.g. scanning) sessions; (c) a quantitative measure, e.g. a quantitative imaging method; (d) known pharmacokinetics; (e) observable clinical reactions such as pain relief or a drug "high."

Without quantitative information some types of clinical information and research goals cannot be achieved. The dose of drug needed by a given patient cannot be estimated except to say that a response is or is not seen to a given test dose. Diagnostic tests cannot be done unless the detection threshold for any response to drug happens fortuitously to correspond to the optimal drug dose response to which best separates ill from healthy tissue. Any response to an intervention, other than an "all or none" response, can not be detected. Progression of disease severity over time cannot be monitored.

On the contrary, the present application acknowledges the lack of existing methods to provide quantitative pharmacodynamic information on responses to drugs and simultaneously map those responses in different regions of an organ or organism. It also acknowledges the lack of satisfactory existing quantitative methods for diagnosis or drug dosage determination by imaging. The present application uses specific pharmacological stimuli and non-invasive imaging techniques with high spatial resolution and gives a solution to said research and medical needs.

SUMMARY OF THE INVENTION

The present invention provides quantitative pharmacodynamic info from a single imaging session with input images that do not need to be quantitative, in response to modest doses of drug. Certain embodiments of the present invention may be used to collect information from normal healthy volunteers, in a very short space of time. Such information is typically useful in designing first (and lengthy) efficacy studies in patients. One example would be identification in a month, from a dozen normal volunteers with one morning's study each, without psychiatric expertise, of the likely dose range to test in an initial phase II 2-month trial of treatment of human volunteers with major depression.

Certain embodiments of the methods and systems described herein include:

1) Collect repeated functional imaging data over time (e.g., BOLD fMRI) of a body function that in some body part changes in response to drug (e.g., midbrain changes in blood flow after an acute dose of levodopa). Perform appropriate motion correction, artifact reduction, filtering, and (if needed) quantification.
2) Give multiple doses of the drug during the time frame imaged, preferably via a rapidly absorbed route. The doses could be equal as we have tested in prior work, or could be unequal (e.g. 0.001 mg, 0.01 mg, 0.1 mg).
3) At each location imaged, fit a pharmacokinetic/pharmacodynamic (PK/PD) model to the imaging time-activity curve over the total scanning period, including as either knowns or (constrained or unconstrained) variables both pharmacokinetic information (e.g., distribution halflife, elimination halflife) and pharmacodynamic information (e.g., relative $EC_{50}$, Hill coefficient). This step is described in detail, below.
4) Identify effect locations, organs or volumes of interest (VOIs) that have the most statistically significant responses, compared to a null hypothesis such as no change, or change that fits a polynomial or other function of time that is unrelated to the experimental design. For example, this may be performed using a ratio of the summed squared error (SSE) after fitting the complete PK/PD model to the SSE after fitting a polynomial with an equal number of parameters to be fit, the ratio can be interpreted as an F statistic. Other possible approaches are obvious to those of ordinary skill in the art.
5) Correction of statistical results for multiple comparisons if multiple volume elements (voxels) are imaged. For example, this may be performed using the methods of SPM2, but other methods are obvious to those of ordinary skill in the art, including ascertainment of typical statistical distributions in biological data and judging significance from this actual distribution. Such methods may better account for the actual distribution in the statistical images produced in the previous step.
6) Extract relative quantitative pharmacodynamic information from the modeling results at each organ, voxel or VOI.
7) If the administered dose is modeled, the results may be quantified in terms of $ED_{50}$ (half-maximally effective dose) or $EC_{50}$ relative to the (unknown) concentration of drug in a body fluid at a given moment relative to administration of the drug. Optionally, by adding measured concentration(s) of drug in a body fluid, the absolute $EC_{50}$ or similar quantitative pharmacodynamic information may be calculated. Pharmacokinetic information also may be computed from imaging data or, for example, from blood concentrations only.
8) The quantitative pharmacodynamic information thus obtained may then be applied to, e.g., dose determination, diagnosis, or treatment planning.

BRIEF DESCRIPTION OF THE DRAWINGS

FIG. 2 is an overview of the pharmacokinetic-pharmacodynamic (PK-PD) model. It includes a time concentration curve for apomorphine in plasma using default parameters (top), with arrows indicating the $EC_{50}$ (concentration that produces half the maximal effect).

FIG. 2 (middle) illustrates the shape of the sigmoid Emax model for the dose response curve on a logarithmic scale.

FIG. 2 (bottom, a) is the BOLD v. time scatter diagram used in determining the $EC_{50}$ indicated by arrow "a" in FIG. 2 (top).

FIG. 2 (bottom, b) is the BOLD v. time scatter diagram used in determining the $EC_{50}$ indicated by arrow "b" in FIG. 2 (top).

FIG. 2 (bottom, c) is the BOLD v. time scatter diagram used in determining the $EC_{50}$ indicated by arrow "c" in FIG. 2 (top).

DETAILED DESCRIPTION

I. Introduction

Figure 1:
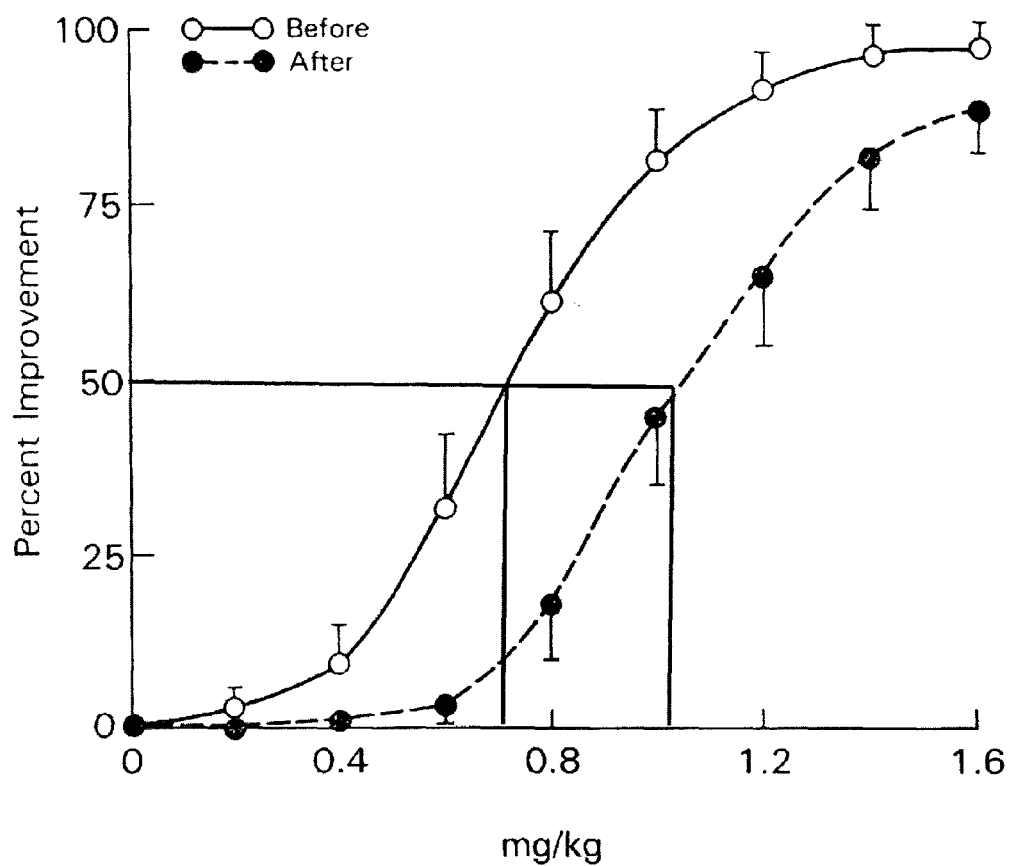
FIG. 1 shows a typical example of a dose-response curve from an unrelated study.

The present invention provides methods and systems that are effective in determining effective drug dosage, diagnosing diseases associated with body organs, including cancers, and the monitoring of treatment of such diseases. This is accomplished through systems that include application of repeated smaller doses of a pharmaceutically active compounds over a brief time interval of minutes such as 2, 4, 5, 10, 15, 20, 30, 45, 60, or 90 minutes, or hours such as 2, 4, 6 8 or 10 hours. The application of a plurality of doses is accompanied by computer modeling allowing the practitioner to calculate relative $EC_{50}$ for the pharmaceutically active compound at any point in a target organ. By further sampling a bodily fluid for drug concentration at any time point including a single time point, the practitioner may calculate a $EC_S$, (e.g., 92 ng/mL).

Thus the present invention provides (1) computation of a pharmacodynamics parameter ($EC_{50}$) along with pharmacokinetic parameters point in brain, (2) multiple doses of drug, and (3) the computer program that does the computation. Moreover, certain embodiments of the present invention allow collection of information in healthy individuals and is particularly useful in situations where drug effects may take an extended time to manifest themselves.

II. Imaging Devices

Imaging devices suitable for use in the present invention are known in the art as any imaging device capable of detecting a visible or physical change in a bodily organ in situ. Examples include PET, SPECT, and functional MRI (fMRI) methods and devices. Visible changes in an organ include necrosis including scarring, color variations, size variations and the like. Physical changes include changes in temperature, density, etc. . . . .

The present invention is suitable for use in monitoring any organ of a body including, but not limited to, heart, liver, muscle, pancreas, ovaries, testicles, bone, cartilage, eyes, kidneys, and preferably brain. Identifiable portions of an organ, or effect sites may also be imaged either separately or in conjunction with multiple effect sites, the organ as a whole, or even multiple organs. For purposes of the present invention, the term "organ" includes effect sites of the organ unless otherwise stated.

III. Acceptable Pharmaceutically-Active Compounds

Compounds suitable for use with the present invention may be any pharmaceutically-active compound that elicits a pharmacodynamic response. Such compounds may be formulated into pharmaceutical compositions using techniques well known to those in the art. Suitable pharmaceutically-acceptable carriers are available to those in the art; for example, see Remington's Pharmaceutical Sciences, 16$^{th}$ Edition, 1980, Mack Publishing Co., (Oslo et al., eds.).

As used herein the language "pharmaceutically acceptable carrier" is intended to include any and all solvents, dispersion media, coatings, antibacterial and antifungal agents, isotonic and absorption delaying agents, and the like, compatible with pharmaceutical administration and do not interfere with the pharmacokinetic or pharmacodynamic properties of the pharmaceutically-active compound. The use of such media and agents for pharmaceutically active substances is well known in the art. Except insofar as any conventional media or agent is incompatible with the active compound, such media can be used in the compositions of the invention.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, polyethoxylated castor oil (CREMOPHOR EL,™ (BASF, Parsippany, N.J.) or phosphate buffered saline (PBS).

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Sterile injectable solutions can be prepared by incorporating the active compound (e.g., a receptor protein or antireceptor antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

It is especially advantageous to formulate oral or parenteral compositions in dosage unit form for ease of administration and uniformity of dosage. "Dosage unit form" as used herein refers to physically discrete units suited as unitary dosages for the subject; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular pharmacological effect to be achieved, and the limitations inherent in the art of compounding such an active compound for the treatment of individuals.

IV. PK-PD Model and Statistical Methods

Theory.

The novel approach depends in part on the recognition that the most accurately measured variable in most imaging experiments is time. By giving repeated doses of drug and measuring responses to each dose over time intervals short enough to minimize time-dependent artifactual signal drift, one can compute a quantitative measure of sensitivity to drug in a single imaging session, even with a nonquantitative imaging method. This process is summarized in FIG. 2. In the upper right panel, a typical time-concentration curve for a drug is plotted using traditional pharmacokinetic modeling (solid curve). The three dashed lines represent three different subjects (or three different tissue regions) with varying sensitivity to drug. Line a represents a region with high sensitivity (low $EC_{50}$), whereas lines b and c represent regions with moderate and low sensitivity. To estimate the expected time-response functions of the various subjects (or regions) requires the composition of the time-concentration curve with the concentration-response curve shown in the middle right graph in FIG. 2. As shown in the lower right panels of FIG. 2, the resultant tissue time-response curves are markedly different. For sensitive subject or region a, the first dose of drug produces a maximal response. For relatively insensitive region c, only the later doses have a substantial effect. The following paragraphs formalize this concept.

The pharmacokinetic-pharmacodynamic (PK-PD) model describes the relationship between the dose of a specific drug and the corresponding effect. This is diagrammatically depicted in FIG. 2 (See Holford, Nicholas H. G., Sheiner, Lewis B. (1982) Kinetics of Pharmacologic Response. Pharmacol. Ther. 16: 143-166). The pharmacokinetic aspect of the model relates the dose of the drug to the concentration of the drug in a compartment, e.g., in plasma or some effect site. The pharmacodynamic aspect of the model relates the concentration of drug in a compartment to the drug effect. The combination of these aspects is the PK/PD model (see FIG. 2).

The invention may be practiced with any number of doses being applied to an individual and/or effect site. At its logical extreme, a single long administration of drug is equivalent to numerous small, brief doses of drug given without interval. By way of an example, four essentially instantaneous IV infusions may be given during a 40-minute phMRI BOLD scan, spaced eight minutes apart beginning 8 minutes after the start of the scanning session. The PK model for these infusions can be described by a simple one-compartment model or by more complex models discussed in any standard pharmacology text. A sigmoid $E_{max}$ model may be used to describe the PD model. The model is characterized by the maximal effect of drug at high doses, $E_{max}$, the Hill coefficient or sigmoidicity index n, which models the number of drug molecules required to activate the receptor and can be understood as describing the steepness of the sigmoid curve at its inflection point, and $EC_{50}$, which for the case n=1 is the drug concentration that produces an effect half as large as $E_{max}$. The middle right graph in FIG. 2 shows this curve on a logarithmic x axis. The input to the curve is plasma concentration of a drug, and the effect that is measured and modeled is the imaging signal.

In the equations below, z(t) describes the plasma concentration of drug when K doses of drug, $D_n$, are given at times $t_n$, and u(t) is the unit step function. The model also includes a fixed time delay (shift) $t_s$ and a halflife $t_{half}$ for loss of drug from plasma. This plasma concentration z(t) then becomes the input to the sigmoid concentration-effect model. To add realism the model also adds drift of signal unrelated to drug input, modeled by a polynomial of degree M, $poly_M(t)$. The sum comprises the model for the imaging signal, here called $tissue_{model}(t)$.

The equations that describe the model are given below:

$$poly_M(t) = \sum_{n=0}^{M} a_n * t^n$$

$$z(t) = \sum_{n=1}^{K} D_n * 0.5^{\left(\frac{t-t_s-t_n}{t_{half}}\right)} * u(t - t_s - t_n)$$

$$tissue_{model}(t) = \frac{E_{max} * (z(t))^n}{(EC_{50})^n + (z(t))^n} + poly_M(t)$$

$$tissue_{noise}(t) = poly_N(t)$$

To best fit the model to the data, we originally used the Levenberg-Marquardt method. This method basically tries to minimize the difference between the real data for each effect site and the given model function by using two other methods for curve fitting, first using the steepest descent method when far away from the minimum error, and the inverse-Hessian method when getting closer to the minimum error (See: Press, William H., Teukolsky, Saul A., Vetterling, William T., Flannery, Brian P. (1988) Numerical Recipes in C++, $2^{nd}$ Ed, Cambridge University Press, Cambridge, UK, pg 688.). The current implementation of the model fitting uses a combination of iteration over selected allowed values in parameter space and ordinary least squares fitting by matrix inversion and multiplication, a method described in section VII below. Other possible parameter estimation methods are obvious to those with ordinary skill in the art.

V. Determining Dosages

The present invention provides methods for determining the effectiveness of pharmaceutically active compounds. For example, the present invention provides rapid methods for determining an effective dose for a pharmaceutically active compound, and is capable of being practiced in this regard on healthy individuals. In another aspect, the present invention allows rapid patient screening to determine whether a particular drug or drug regime (cocktail of two or more pharmaceutically active compounds) will be effective in treating individual patients. E.g., the present invention may be used to determine which anticonvulsant would be effective and at what estimated for a given patient. Finding correct effective medications and dosages are especially critical where the medication is expensive, toxic, or essential for preserving life. Rapid determination of correct effective dosage is also important where under- or overshooting the dosage would be dangerous or where clinical effect would take weeks to monitor (e.g. antidepressants).

In the present invention, effective medications and dosages are determined by administering a plurality of doses of pharmaceutically active compound to a patient. The patient may be a healthy individual or a sick one. Time course imaging of a target organ or effect site is then performed and alterations in a detectable property of the target organ monitored. From these observations an $EC_{50}$ for the administered pharmaceutically active compound may be determined as described herein and an effective dosage calculated.

A second exemplary approach involves tracking therapeutic progress during treatment. For example, Parkinson's disease treatment usually involves administration of L-DOPA, the precursor of the neurotransmitter Dopamine (DA), sometimes combined with substances that block peripheral conversion of L-DOPA to DA. Although L-DOPA replacement therapy has proven to be very efficacious, it is difficult to optimize the dosage. Too high dosing may lead in the short term to dyskinesia, while in the long term it may even accelerate the degradation and loss of DA neurons. Optimization of the dose by neurological examination alone is a time-consuming and possibly dangerous approach. The present invention allows monitoring of dosage and effect in a manner that circumvents such difficulties. This is described in detail in the example below. Briefly, through short term monitoring of brain voxel sites known to respond to L-DOPA, an effective dose for the drug may be determined without risking dangerous over or under dosing or delaying effective treatment. Individual screening is an important aspect of this embodiment of the invention as it is certain that individual patients will show a different response to the various drugs, and it may be impossible or impractical to determine the optimal treatment for each patient by clinical examination alone. The present invention offers a quantitative, objective and efficient way to compare the efficacy of various drugs in the treatment of PD.

An additional example is provided by the problem of choosing an appropriate first dose(s) for an early Phase treatment study of major depression. Although tolerability can be estimated from Phase I studies, estimating the approximate population efficacious dose from preclinical studies or from normal humans is fraught with difficulty. A clinical study requires at least 6-8 weeks per subject and often takes over a year to complete. Estimation in healthy or depressed subjects, in a single imaging session, of the $EC_{50}$ of a metabolic or hemodynamic regional brain response to modest (below $EC_{50}$) doses of drug by the method described above could potentially shorten the development cycle substantially. Furthermore, if healthy and depressed subjects have similar acute brain tissue imaging responses to drug, determining the approximate dose for an initial Phase II study could be determined without the need to recruit ill subjects and without psychiatric expertise for subject selection and response monitoring.

Again such dosage determinations are not limited to any particular tissue. For example, a vasodilator drug may be assessed by imaging coronary artery diameter in vivo during drug infusion.

VI. Diagnosis

The present invention may also be used in detection, diagnosis and guidance of therapy involving a diseased organ, and is particularly useful in neurological, neurodegenerative, and psychiatric disease diagnosis. Such diseases include but are not limited to, Parkinson's disease (PD), Alzheimer's disease (AD), Huntington's chorea, and schizophrenia. By way of example, PD is associated with loss of dopaminergic neurons and is known to remain asymptomatic for a prolonged period. Often clinical symptoms are only observed after 70% of the dopaminergic innervation has been lost. By measuring voxel changes, for example, in the brain in response to a dopaminergic agonist such as amphetamine, asymptomatic individuals may be identified at a stage of disease progression where treatment may substantially extend the patient's quality of life. The feasibility of such an approach is demonstrated in the example below in human subjects.

As another illustrative example, the method can equally well be applied to diagnosis, staging and guidance of therapy of Alzheimer's disease which affects four million people in the US alone. As already mentioned, successful application of PET is hampered by the high cost and the requirements for cyclotron and technical support. Measurements of rCBF by SPECT, on the other hand, have been found to be "of limited application for identifying mildly demented AD patients, . . . and of limited value for distinguishing moderately to severely demented patients with AD or vascular dementia" (27). Although success of therapeutic treatments of AD is, at present, still limited, early diagnosis is nevertheless important (a) in order to rule out other causes like tumors or stroke which might be treated successfully and (b) because the few therapeutic agents known today work best in the early stages of the disease.

When supplied with the disclosure provided herein, it will be obvious to one of skill in the art that the applications to diagnosis described herein may be applied in an analogous manner to any tissue where a drug/tissue reaction combination is known in the art and associated with a disease state of the tissue responsive to the drug.

VII. Computer Method

Figure 3:
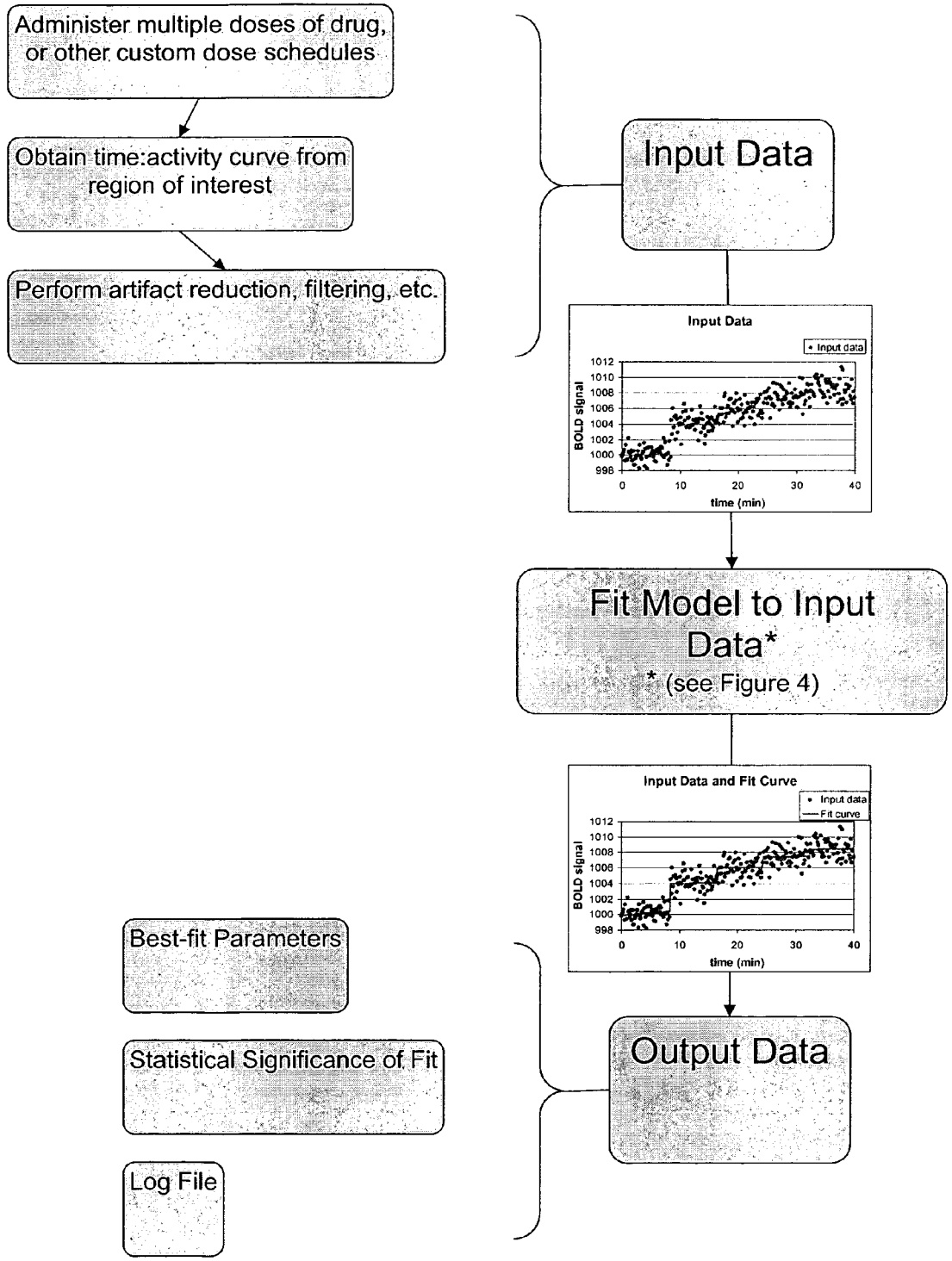
FIG. 3 is an overview of the computer program in the form of a flow chart.
Figure 4:
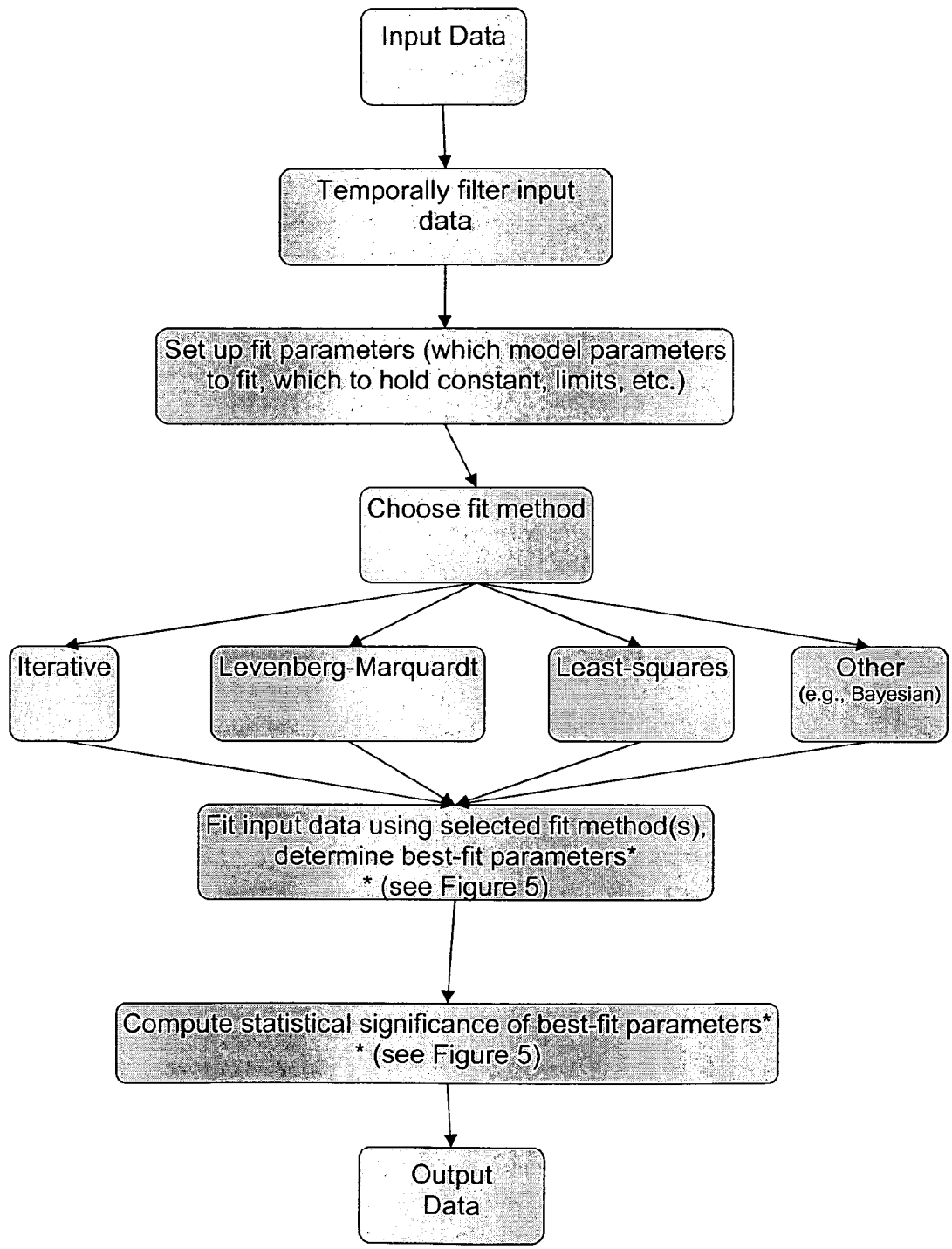
FIG. 4 is a flow chart describing the process of fitting input data to a model.

The computer method determines quantitative pharmacodynamic parameters from biological data when such data are acquired during a pharmacological activation experiment involving administration of various doses of drug (see FIGS. 3 and 4 for overview). As built, this method can be applied to any time-series biological data, though it is optimized for data from an imaging system. The method involves the combination of several components described below. For brevity, and because they are not essential characteristics of the method, obvious steps such as reading data from a disk file into memory or writing results to disk are omitted.

Figure 5:
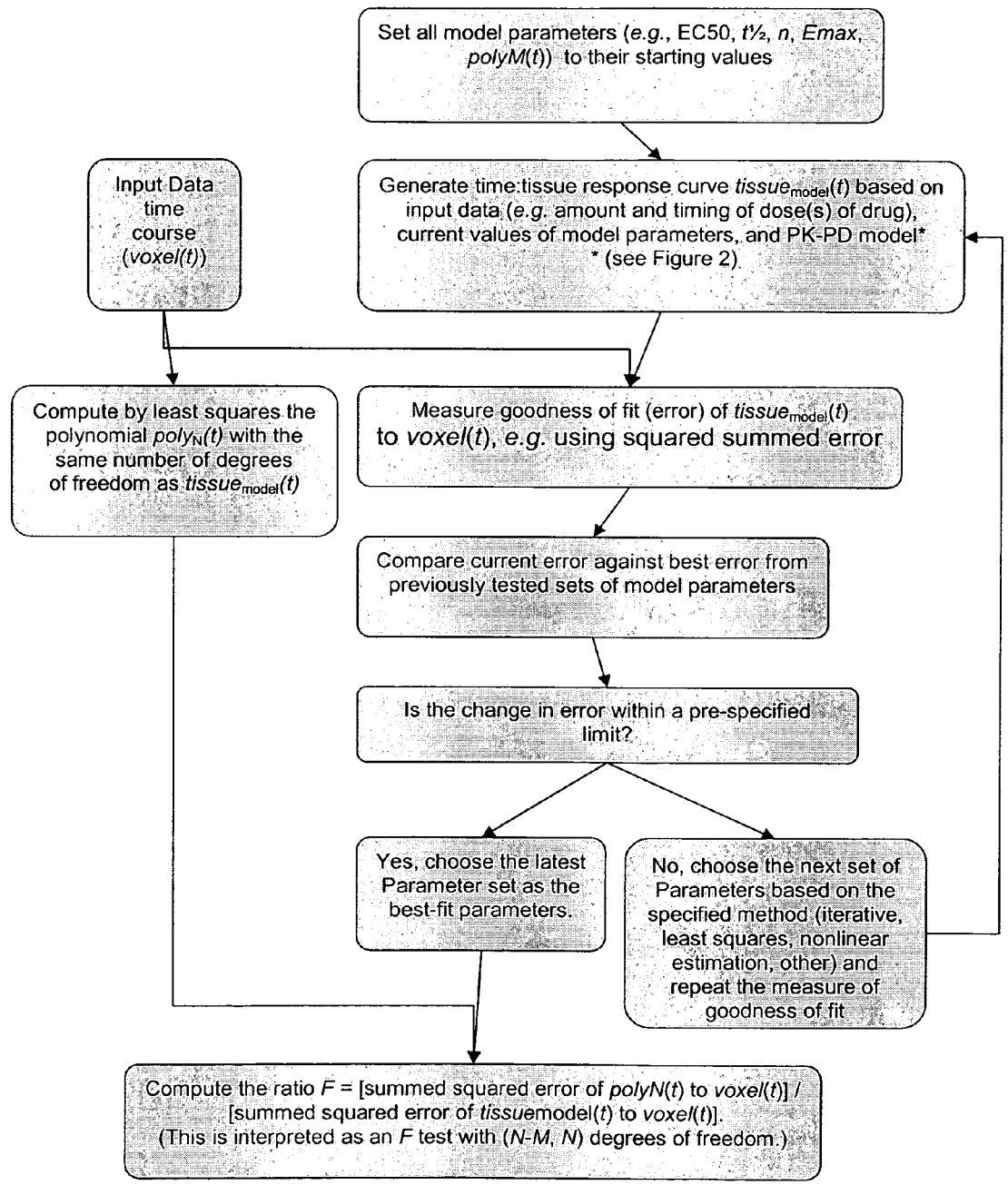
FIG. 5 is a flow chart describing the process of finding best-fit parameters for the input data.

The program includes a module that predicts the blood concentration over time, C(t), in response to a supplied description of the times and quantities of administered doses of drug and a standard one-compartment pharmacokinetic model as described in section IV above (see FIG. 5). The predicted function C(t) also includes a variable delay to account for nonzero administration times or noninstantaneous absorption, or to partially account for hysteresis.

The program also predicts the response of the tissue or organism to varying blood concentrations of drug, E(C), using a typical sigmoid pharmacodynamic model as described in section IV above.

The composition of these two functions, E(C(t)), varies depending upon the supplied dose administration details and the values supplied for the various pharmacokinetic and pharmacodynamic model parameters described above, such as Emax, $EC_{50}$, the Hill coefficient n, the elimination half-life, the time delay, and so on.

The program also allows the user to select which model parameters will be held constant and at what values, and what will be the starting values and allowable range of the remaining (fit) parameters.

To compare two possible one-dimensional functions of the time variable, as sampled discretely over the time interval given, the program computes an error function, either the chi square error function or the summed squared error. This error or cost function is used to measure the goodness of fit of the prediction E(C(t)) to the actual supplied biological data, with better goodness of fit being reflected by lower error.

The program samples parameter space and minimizes error by adjusting the parameter values within their allowable domains using any of three methods. An early version of the program used a nonlinear curve fitting algorithm as described in Section IV above. Subsequent applications of this program to simulation data revealed that this method did not perform better than the method described next. For all parameters but Emax and the polynomial terms ("iterated parameters"), the program iterates over a discrete set of values representative of each parameter's allowed domain. Approximately eight to 10 values provide adequate sampling for each parameter but this could of course be varied. Using these parameters the predicted shape of E(C(t)) is computed using $E_{max}$=1. For convenience call this result $E_1(C(t))$. The program then determines the value of $E_{max}$ and of the polynomial coefficients $a_i$ that optimally fit the predicted full PK-PD model $$a_0+a_1t+\ldots+a_nt^n+E_{max}\cdot E_1(C(t))$$

to the provided biological data. This is done exactly by the method of ordinary least squares using matrix inversion and multiplication; algorithms for these methods are given in many standard numerical methods texts. The cost function is then computed for each set of parameter values. The set of values for the iterated parameters that minimized the error function, over all allowed combinations of these parameters, is identified as the optimal set of values and returned to the user. Other methods of optimizing the iterated parameters will be obvious to those with ordinary skill in the art.

The program also computes a statistic that quantifies the goodness of fit of the full PK-PD model to the provided biological data. Several possible methods for statistical model comparison have been described. The current implementation uses the following approach. The number of PK-PD model parameters chosen to be fit to the data by the user is added to the degree of the polynomial described in the preceding paragraph. Call the sum m. A polynomial of degree m is optimally fit to the supplied data, again using least squares methods to provide the exact solution. Note that this polynomial has the same number of free parameters (m) as the full PK-PD model. The squared error at each time point represented in the provided data, summed over all such time points, is summed for the full PK-PD model computed as described in the preceding paragraph and also for the best-fit polynomial of degree m. The ratio (summed squared error for polynomial)/(summed squared error for best-fit full model) is reported to the user and is interpreted as an F statistic with m and [(number of time points sampled in the provided biological data)−m−2] degrees of freedom.

Figure 6:
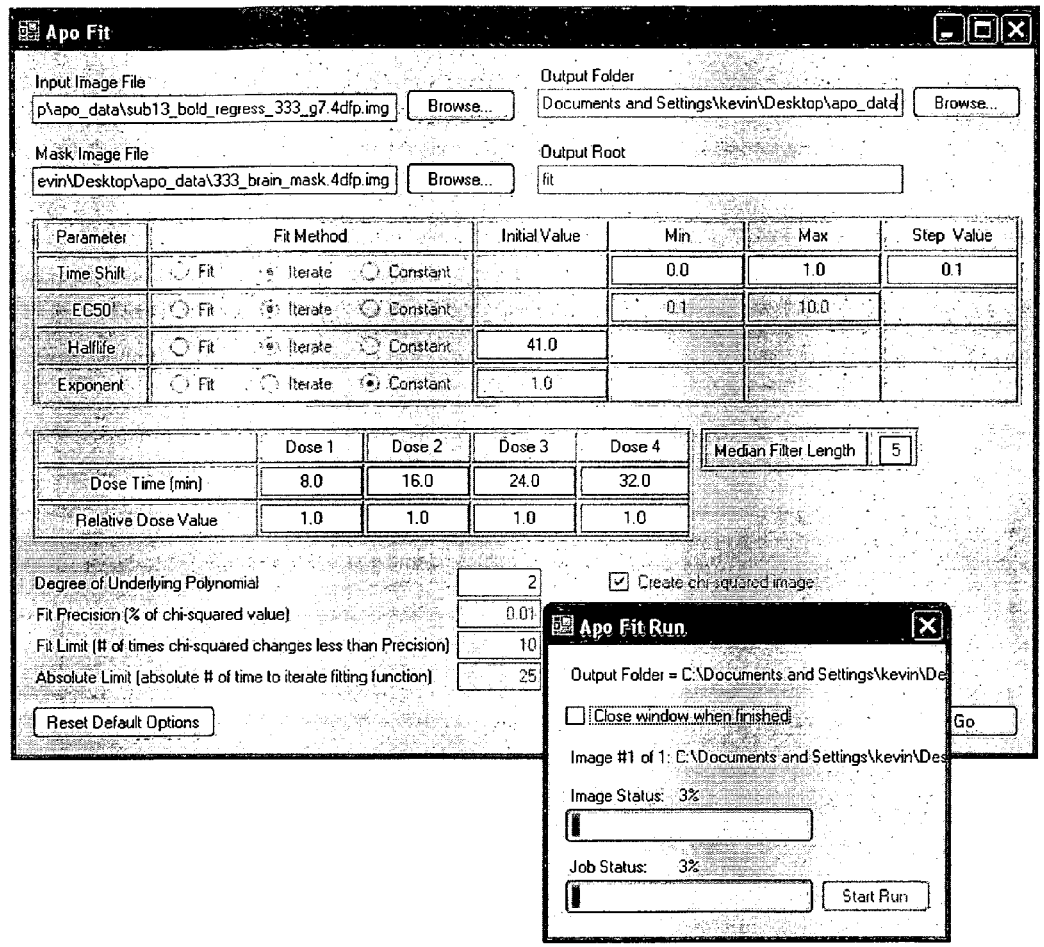
FIG. 6 here is a screen shot of the program running, with the setup screen in the background and the status in the foreground. The program can be configured to fit each parameter, or iterate through any or all of them as is necessary to practice the invention.

The computer program supplied in the appendix (on CD-ROM) is a working model of this method (see FIG. 6). It was written and compiled using Microsoft Visual Basic and is operable on a computer using a Pentium or compatible processor and the Microsoft Windows XP operating system with .NET version 2.0. The program prompts for image files supplied in the "0.4dfp" format, which is a widely used floating point ANALYZE-compatible four-dimensional image "multivolume" with details represented in the Interfile Header Format (.IFH) files, ANALYZE header files, and images available at http://www.purl.org/net/kbmd/b2k/. Other options set by the user are obvious to those with ordinary skill in the art.

VIII. Systems

The present invention also provides systems for carrying out the methods described herein. Typically such systems include an imaging device for observing the tissue under study and a computing device for performing the calculations necessary to model the system and/or determine effective dosages for pharmaceutically active compounds under study. The appendix to this application provides exemplary computer code for carrying out such calculations, for example on a personal computer. The present invention contemplates other implementations of the method described herein, and as such the computer code presented in the appendix should be considered exemplary only and not limiting on the present invention. For example, other computer languages and platforms may be employed. In addition, other arrangements of procedures and functions may be used to accomplish the present invention.

EXAMPLE 1

Introduction

We tested the performance of the methods and system described in this application using simulated data.

Predicted time-imaging curves $\text{tissue}_{model}(t)$ were generated for a wide range of plausible values for $EC_{50}$, half-life, and other PK-PD model parameters. A value of $E_{max}$=10 was used for all simulations. Gaussian noise was added to $\text{tissue}_{model}(t)$ to better reflect real-world situations. A random noise function of time was generated 1000 times for each level of noise (quantified as the standard deviation of the noise for comparison to the known $E_{max}$) to allow testing of sensitivity and specificity of the curve-fitting methods.

Figure 7:
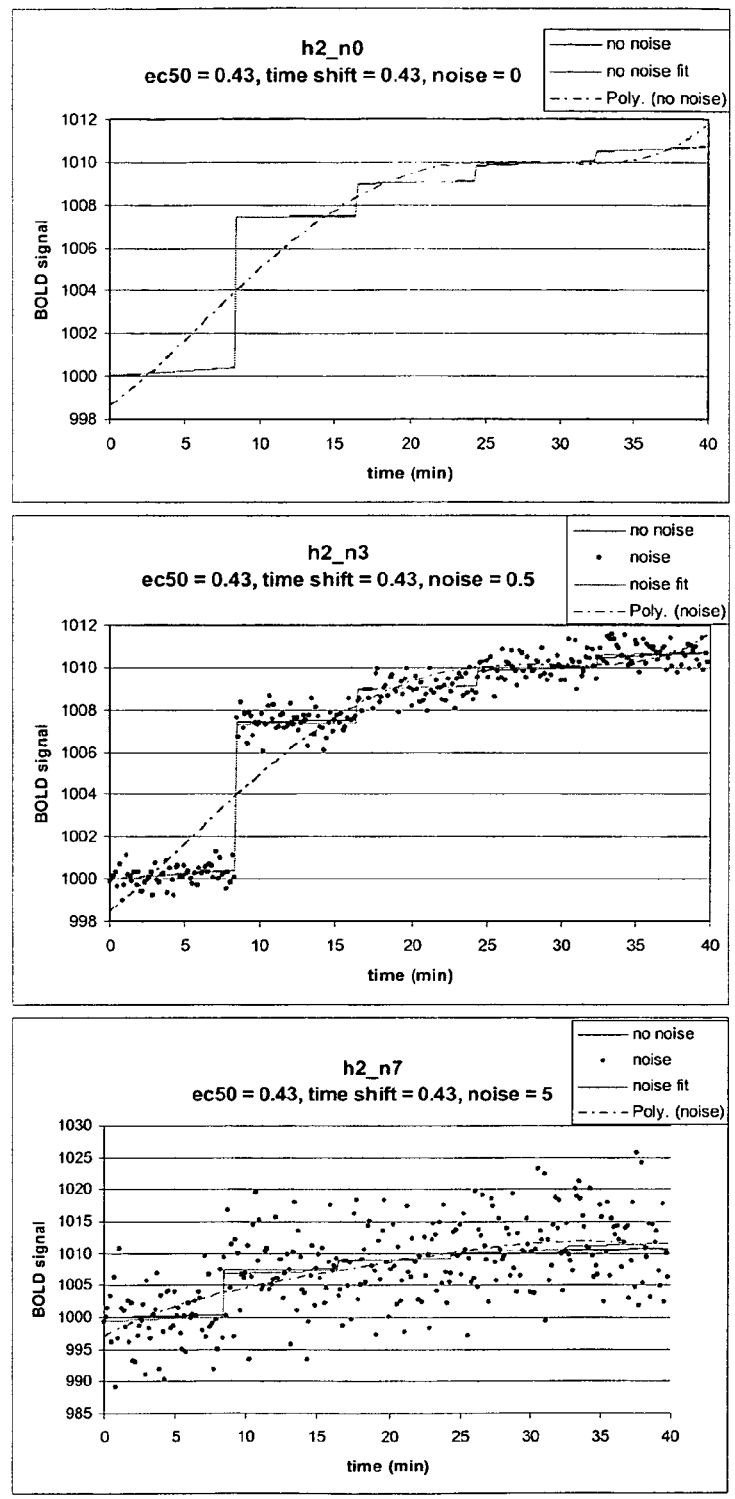
FIG. 7 provides an example of a simulated BOLD time course, both ideal (solid line) and with increasing noise (dots).

FIG. 7 shows examples of $\text{tissue}_{model}(t)$ (solid line) and the sum of $\text{tissue}_{model}(t)$ and noise (dots) for different levels of noise. It is apparent that at high levels of noise, curve fitting will be difficult.

To test how likely the curve-fitting procedure was to report a fit to data in the absence of an (intentional) signal, noise was also repeatedly generated and added to a polynomial of low degree. Without noise the algorithm could not fit another curve better than the polynomial and F should always be low. With substantial noise, however, the resulting data may be fit better by another curve such as that generated by the model.

Parameter Estimation

Parameters were estimated using the computer method described above in this specification. Data first were filtered temporally to minimize noise, replacing the data at each time point with the median of the data acquired over a longer interval centered on that time point. For the data described here a 45-second interval was used.

For the simulation testing described below, we divided predetermined ranges of each PK-PD model parameter into approximately 10 levels each to simplify testing. In other words, the program could produce only certain answers (e.g., $EC_{50}$ could be only a set of specified values between 0.1 and 10). These values were appropriate to the range of input data supplied the program during simulation testing. This quantization was felt to be reasonable since in practice precision is most important if the $EC_{50}$ is within an order of magnitude or so of the achieved blood concentration; values outside that range tend to have similar minimal effect or similar maximal effect. For testing, the desired ("correct") answer was chosen to be a value not available to the program, e.g. 0.43, so as not to favorably bias the results. For the data shown here, halflife was fixed (not fit) and the Hill coefficient n was set to 1.

Statistical Test of Goodness of Model Fit to Simulated Data

Summed squared error across all time points at a given voxel was used to quantify how well the data at the voxel, voxel(t), were fit by a given time-activity curve $tissue_{model}(t)$ generated by the PK-PD model and a given set of model parameters. A comparison function that did not incorporate any information about drug administration was used to statistically test how well the model fit the data. For simplicity the comparison function chosen was a polynomial with the same number of degrees of freedom as the PK-PD model $tissue_{model}(t)$. Specifically, if k PK-PD model parameters were used to generate z(t), to which a polynomial of degree M, $poly_M(t)$, was added to give $tissue_{model}(t)$, the comparison function was $poly_N(t)$, where N=M+k. The ratio F of the summed squared error for $poly_N(t)$ to the summed squared error for $tissue_{model}(t)$ is computed and saved to create a statistical image reflecting the improvement in the fit to the data by incorporating knowledge of drug administration times and the PK/PD model. Higher values for F indicate better fit for the model. Probability that the model fit better than the comparison polynomial by chance was computed by interpreting F as an F test statistic with k and ([number of time points in voxel(t)]−k−2) degrees of freedom.

Simulation Testing: Test Statistics

For each combination of parameters tested, the model was fit to 1000 voxels at each noise level. The following summary statistics were obtained for each set of parameters and noise level:

mean and range for F and each of the fit model parameters ($EC_{50}$, n, $t_{1/2}$, etc.)

sensitivity=fraction of times (of 1000) that the primary parameter of interest ($EC_{50}$) returned by the program was "correct" i.e. if the value of $EC_{50}$ used to generate the data was 0.43, and the possible answers included {0.10, 0.50, 1.0, . . . }, then only the nearest possible answers, 0.10 and 0.50, were counted as correct. In other words, how often does the program return as close as possible to the desired value?

positive predictive value (PPV) was defined as follows. A given allowed output value of $EC_{50}$ could have been returned by the program from input generated from a different $EC_{50}$ value plus noise. The PPV was computed with denominator equal to the number of times that the given $EC_{50}$ value was output by the program across all sets of 1000 voxels generated by all sets of input model parameters, and numerator equal to the number of those times when the output was the "correct" answer for the input. In other words, for an $EC_{50}$ output value of 0.5, of all the times the program output $EC_{50}$=0.5, what fraction came from an input $EC_{50}$ value nearer 0.5 than any other output value?

It should be noted that PPV depends on the prior probability, i.e. how often the specified output value was supposed to be produced, so the actual PPV in a given experimental situation may differ from that computed here. However, the PPV can be computed from prior probability, sensitivity and specificity when these are known. The first two of these are described above. Specificity was computed from the (polynomial+noise) data, and was taken to be 1−p, where p is the likelihood (fraction of times in 1000 attempts) that the program returned a given value for $EC_{50}$. Specificity for F was defined similarly as one minus the likelihood in the (polynomial+noise) data that F exceeded a given threshold.

Results: Model Fitting

Figure 8:
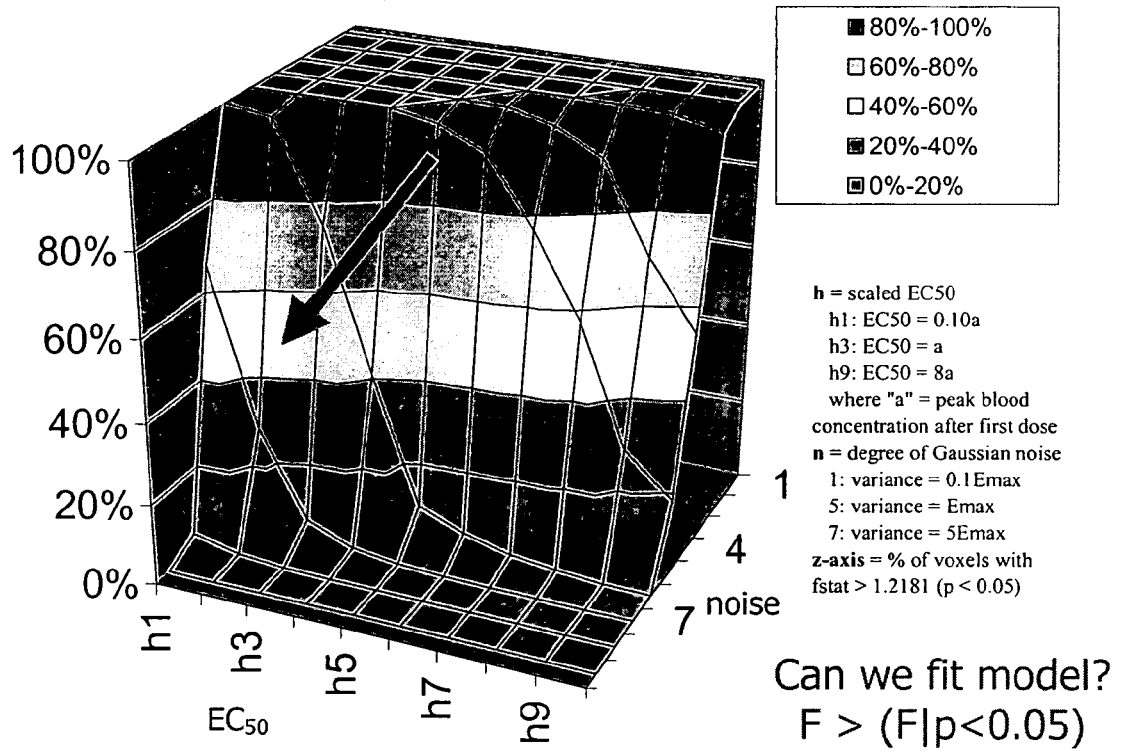
FIG. 8 shows predicted sensitivity from validation data, varying by noise and input $EC_{50}$.

FIG. 8 shows how often the model fit the curve significantly better than did the polynomial comparison function. As visible in this figure, the model fits better essentially all the time unless the noise level is quite high. Even in the presence of substantial noise, the model also fits better for sensitive regions (i.e. low $EC_{50}$).

Figure 9:
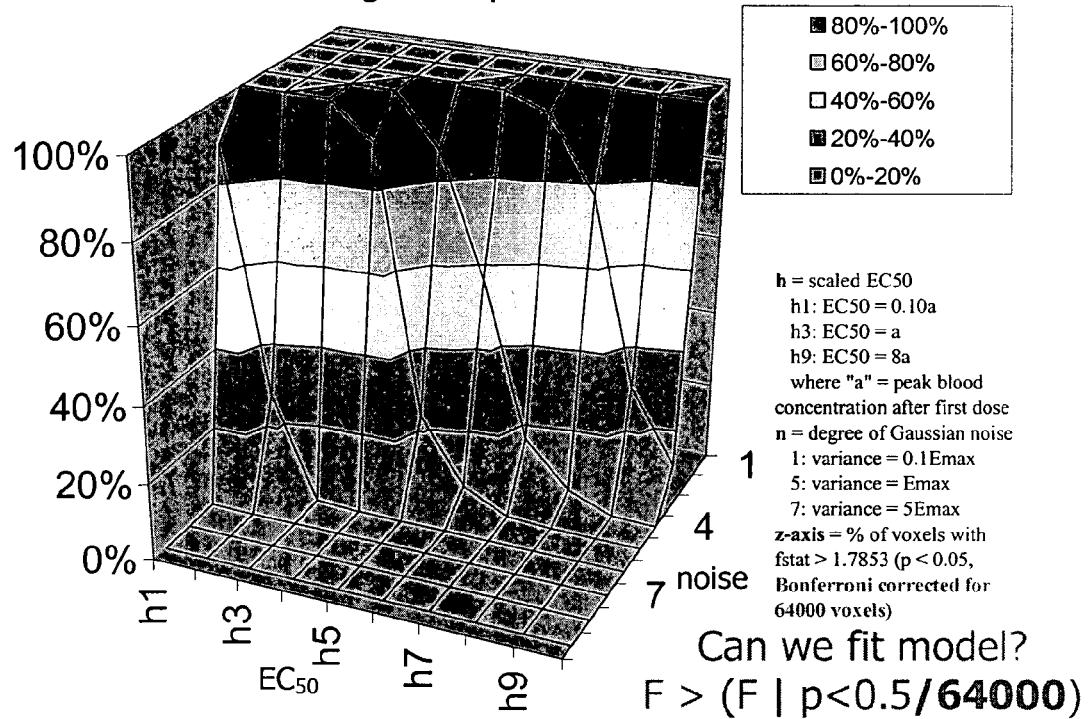
FIG. 9 also shows predicted sensitivity from validation data, but with a more stringent statistical threshold.

FIG. 9 uses a more stringent statistical threshold for F corresponding to the Bonferroni correction for a typical number of voxels in a brain imaging experiment (64,000). The same descriptive results obtain.

Specificity: The model never produced a significantly better fit to the null hypothesis (line plus noise) data, i.e. specificity=1.0 for this data set.

Results: Correctness of $EC_{50}$ Estimate

Figure 10:
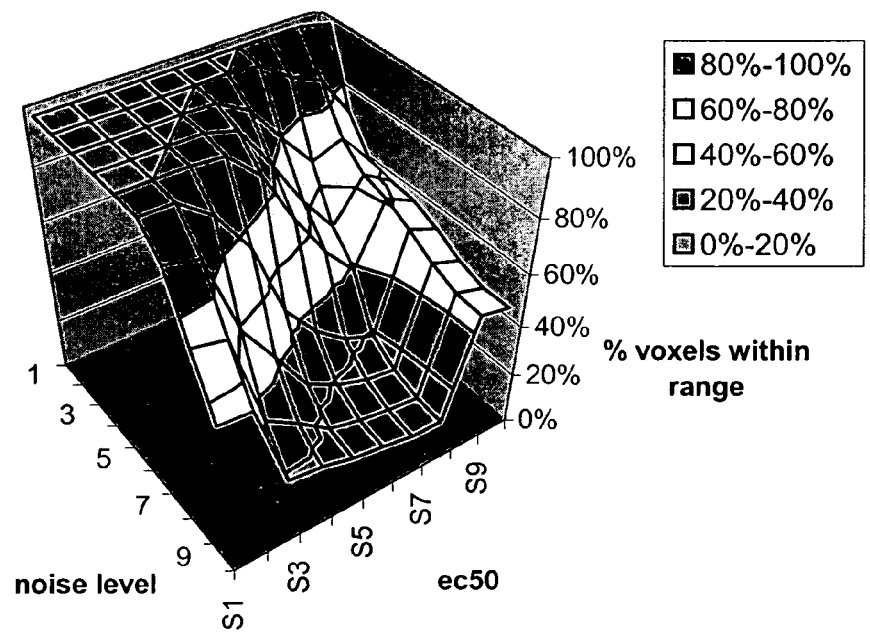
FIG. 10 shows the percentage of voxels within range of the correct input $EC_{50}$ for varying noise levels.

FIG. 10 shows on the vertical axis the percent of voxels in range of the desired (input) value for $EC_{50}$, as a function of input $EC_{50}$ and noise level. The program found the correct value 100% of the time for low levels of noise or for low $EC_{50}$ values. The sensitivity remained high except at high levels of noise or for voxels with low sensitivity.

Figure 11:
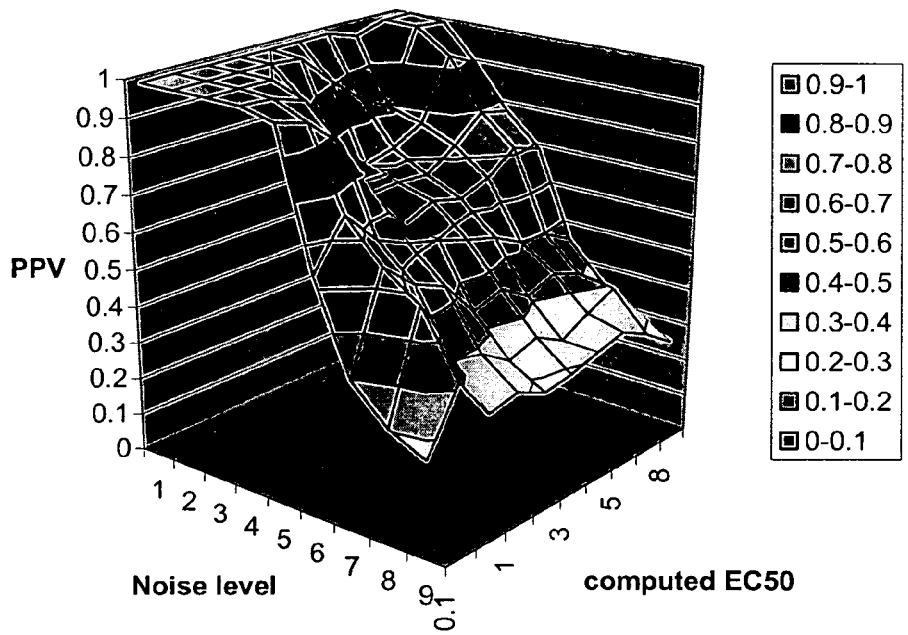
FIG. 11 shows the positive predicted value (PPV) for varying noise levels and input $EC_{50}$.

FIG. 11 shows positive predictive value (PPV) on the vertical axis. This figure demonstrates that, of all input time courses for which the computer program returned a given value for $EC_{50}$, most were in fact generated using that value for $EC_{50}$. Positive predictive values were 100% for regions with low noise or high sensitivity. A very similar pattern was seen when examining only voxels for which the model fit substantially better than the comparison polynomial (data not shown).

Summary

If the modest assumptions of the method are met, the novel method performs very well even with modest levels of noise. Confidence is justifiably high that regions identified as being of high sensitivity of drug are in fact so. The assumptions are reasonable and are iterated here. (a) The sigmoid pharmacodynamic model is appropriate for a given drug and imaging measure. (b) Artifactual signal drift is reasonably approximated by a low-degree polynomial. (c) Measurement error approximates a normal curve.

EXAMPLE 2

To determine how the noise levels in the simulation data just described correspond to realistic biological data, we acquired data using BOLD-sensitive fMRI imaging of an anesthetized monkey with administration of the dopamine agonist SKF82958.

Experiments were approved in advance by the Washington University Animal Studies Committee and due care was exercised to prevent discomfort to the animal. During imaging sessions the animal's health was monitored by veterinary staff from the Washington University Division of Comparative Medicine. Two male *M. fascicularis* monkeys were studied.

Imaging was done while the animals were ventilated with 1.5% isoflurane in oxygen.

We obtained repeated whole-brain BOLD-sensitive fMRI images at a repetition interval of one every 3 seconds over a 40-minute period.

At 10 minutes into the imaging session a steady-rate, slow intravenous infusion of the dopamine D1 agonist. SKF82958 was commenced finishing at 15 minutes, with a total administered dose of 0.1 mg/kg. We have previously shown that this dose of drug is safe and does not affect whole-brain mean quantitative blood flow, but produces reliable effects on regional blood flow consistent with local neuronal activation (Black et al, J Neurophysiol 2000; 84(1):549-557).

Volumes of interest (VOIs) were traced on structural brain images acquired at the same session. These included left and right caudate, left and right putamen, striatum collectively, whole brain, and a midbrain region. Time-activity curves from each VOI were extracted and submitted to the computer method described above.

Figure 12:
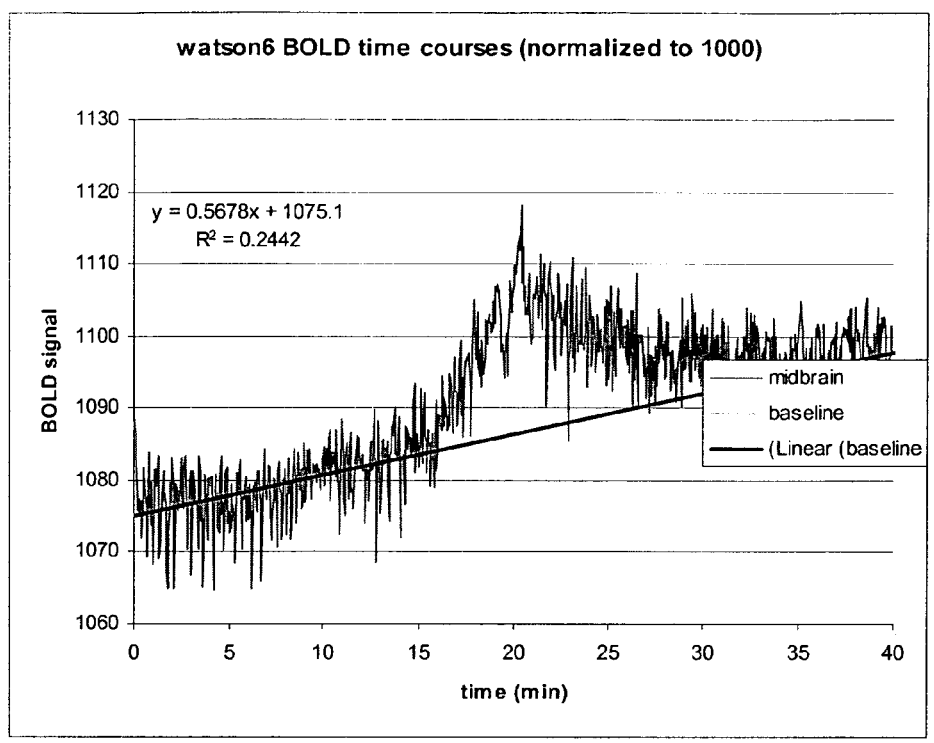
FIG. 12 shows a time-activity curve for one volume of interest in one subject.

A time-activity curve for one VOI in one subject is shown in FIG. 12. From this figure it is seen that $E_{max}$ with this experimental system is of magnitude at least 20. A straight line was fit by the method of least squares to the VOI data from the first 15 minutes of the experiment, i.e. before any drug was administered. The standard deviation (S.D.) of the residual signal after subtracting this line from the data was computed. Across different VOIs and the two subjects, this standard deviation varied from 0.21 to 3.33. The S.D. for all striatal regions was in the range 0.97-2.09.

Figure 13:
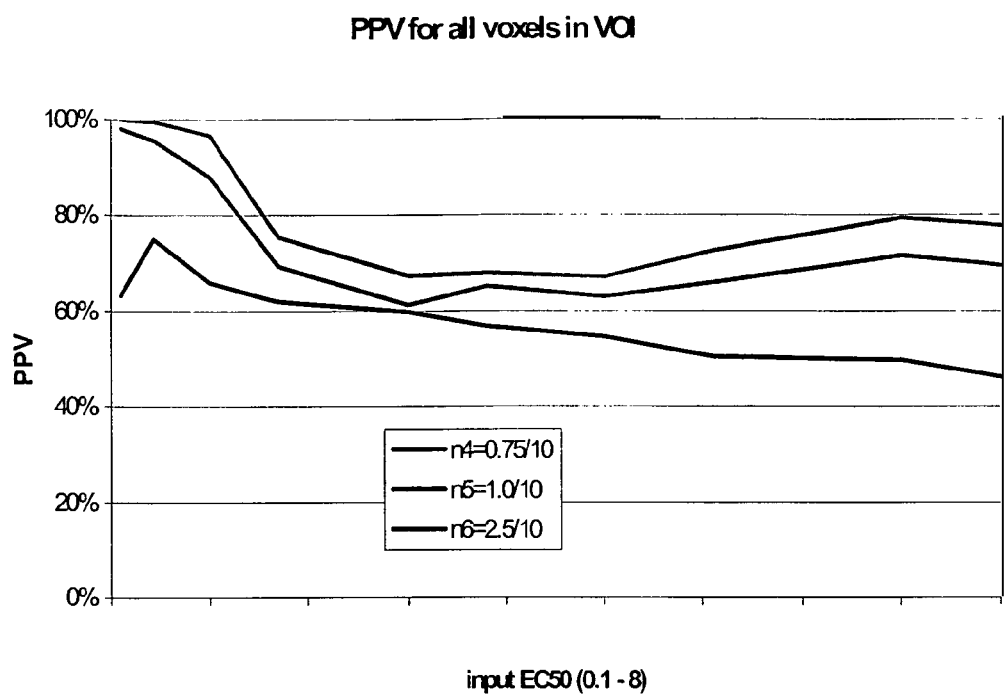
FIG. 13 shows three positive predicted value curves for three noise levels that are similar to the noise levels in the time course of FIG. 9.

Since $E_{max}$>20, the ratio S.D./$E_{max}$<S.D./20. This ratio was computed and compared to S.D./$E_{max}$=S.D./10 for the simulation experiment. Thus in the worst case ($E_{max}$=20), a typical striatal region with S.D.≈1.5 corresponds to the fourth lowest noise level in the simulation data, which had S.D./$E_{max}$=0.75/10. The positive predictive value for this level of noise, depending on the input $EC_{50}$ value, is shown as the middle of the three curves on FIG. 13. The upper and lower curves on this figure correspond to S.D./$E_{max}$=0.5/10 and S.D./$E_{max}$=1.0/10 respectively.

In summary, using real biological data, the noise level and effect size seen with an appropriate pharmacological stimulus, combined with the results of the simulation testing data, suggest that there is high confidence in the $EC_{50}$ values returned for regions identified as having high sensitivity to drug (low $EC_{50}$) by the methods and systems described in this application.

EXAMPLE 3

Introduction

This example describes the implementation and testing of a pharmacokinetic-pharmacodynamic model for analysis of functional MRI data. The data illustrates mapping and quantifying a brain BOLD response to an acute dose of apomorphine in living humans.

Many important neurological and psychiatric illnesses involve abnormalities of dopamine function. An in vivo method to measure dopaminergic system sensitivity would benefit diagnosis and research. Positron emission tomography (PET) has been used, to measure regional cerebral sensitivity to dopamimetic challenges, but PET is not ideal for longitudinal studies or for research in children.

Methods

Regulatory Approval

Approved by FDA (IND #62999, 63000) and WUSM Human Subjects Committee (IRB). Subjects gave written informed consent.

Study Population.

6 normal control and 9 Parkinson's disease (PD) patients were selected to participate in the study.

Study Day Overview

The PD patients attended one MRI day on which they were given an apomorphine challenge. The normal control subjects took part in two MRI visits: an apomorphine challenge and a saline control day. Domperidone was given at 20 mg p.o. q.i.d. for 6 doses, with the last dose given 30-60 minutes prior to the administration of apomorphine. IV catheters were placed in arm veins for infusion of apomorphine (total dose, 10 µg/kg) or a saline placebo. Apomorphine was given during a 40-min fMRI session, as described below. Afterward, subjects were asked to rate any side effects on visual analog scales.

MR Methods

Anatomic images and BOLD sequences were obtained using a 1.5T Siemens Visions system equipped with boosted EPI gradients. Asymmetric spin echo provided BOLD-sensitive images [Hershey et al. Biol Psychiatry 2004; 55(9):916-925].

Pharmacologic Challenge

Four i.v. infusions were given during the 40-minute phMRI BOLD scan. Each consisted of 0.0025 mg/kg apomorphine given over 30 seconds. They were given at 8, 16, 24, and 32 minutes into the fMRI session (see top of FIG. 2).

PK-PD Model

Apomorphine pharmacokinetics were described by a 2-compartment linear model with variable parameters. FIG. 2 (top) shows a time/concentration curve for apomorphine in plasma using default parameters. We used a sigmoid concentration-response curve to describe pharmacodynamics (middle of FIG. 2). FIG. 2 (bottom) shows the predicted BOLD response to apomorphine, plus gaussian noise, given three different values for $EC_{50}$ (concentration that produces half maximal effect).

The following parameters were estimated from individual voxel time:BOLD curves by an iterative least-squares fit method.

TABLE 1

| PK/PD parameters fit using custom software | |
|---|---|
| Parameter | Starting value |
| Ratio of $EC_{50}$ to first plasma peak | 2.0 |
| Elimination halflife of apomorphine | 41.0 min |
| Time delay from plasma peaks to BOLD peaks | 0 sec |
| Line or polynomial coefficients, $a_i$ (in $a_0 + a_1 x + a_2 x^2 + a_3 x^3$) | 0 |
| Peak difference between data and polynomial ($E_{max}$) | 0 |

Image Analysis

We examined two models of brain BOLD signal under the null hypothesis of no drug-related activation: (1) straight line drift; (2) cubic polynomial. Each was compared with the best-fit curve described by the variables in Table 1. The ratio F of summed squared error was used to quantify variance better explained by the full model than by the line or polynomial.

Results

Analysis of Apomorphine Scans.

Figure 14:
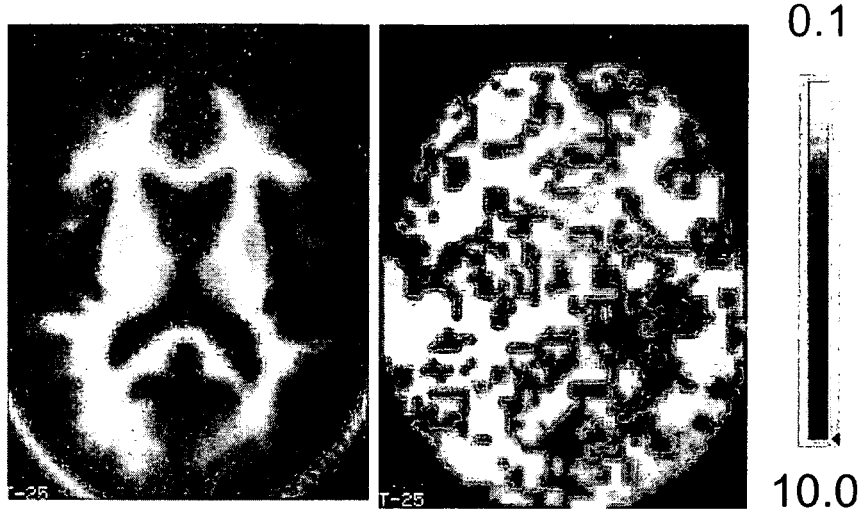
FIG. 14 shows one slice through an example EC50 image (right), and a corresponding anatomy image (left).

A typical $EC_{50}$ image is shown in FIG. 14. Testing continues at this date to determine how accurately this method differentiates healthy subjects from Parkinson disease patients and how consistently high-sensitivity (low $EC_{50}$) regions are identified across subjects.

Conclusions

We have been able to implement a PD/PK model for analysis of fMRI data. By giving repeated small doses of drug, the timing of any brain response can be expected to depend on the sensitivity of that brain region to drug. For instance, a region with high sensitivity to drug may show a maximal response beginning with the first dose, whereas a region with lower sensitivity to drug would show a response only after repeated doses, or not at all. In other words, this method potentially converts an unknown pharmacologic parameter ($EC_{50}$) to a measurable variable (time course of BOLD signal).

Since the blood arriving at all parts of brain has essentially identical concentration of the test drug, the relative sensitivity of different regions of brain can be directly compared. If additionally one can measure the concentration of the drug in blood, the relative sensitivities can be quantified, e.g. the $EC_{50}$ (concentration that produces half-maximal effect) can be computed and given in ng/mL. The method could be applied to many other drug challenges. Future refinements may include higher doses of apomorphine, better curve-fitting, or more quantitative MR methods such as arterial spin labeling.

ADDITIONAL EMBODIMENTS

The methodology of any of the methods or the system discussed above may be further enhanced in various ways. One such way would be to add explicit hysteresis modeling to the dose response of the pharmaceutically active compound by adding an effect site delay compartment to the pharmacokinetic-pharmacodynamic model. Such an enhancement would take into account the dose response effects of drugs such as levodopa, whose biological effect at a given moment reflects not only the current blood level but also recent blood levels. Additional improvements whose implementation will be straightforward may include more complex pharmacokinetic modeling, e.g. a two-compartment model with distribution and elimination modeled separately, or more complex pharmacodynamic modeling. Long single-dose infusions can be modeled by these methods and system and are distinct from prior art in the method used for analysis. Additionally, equal timing and amount of doses is not required by the methods or system taught here. The computer method is not limited in application to imaging data or drug-effect modeling but could equally characterize drug-receptor binding ($K_D$) or perhaps enzyme kinetics.

Although the foregoing invention has been described in some detail by way of illustration and example for clarity and understanding, it will be readily apparent to one of ordinary skill in the art in light of the teachings of this invention that certain changes and modifications may be made thereto without departing from the spirit and scope of the appended claims.

All publications and patent applications cited in this specification are herein incorporated by reference as if each individual publication or patent application were specifically and individually indicated to be incorporated by reference.

What is claimed is:

1. A method for determining quantitative pharmacodynamic parameters for a pharmacologically active agent in a biological organism, the method comprising:
    a) administering to a biological organism a plurality of doses of the pharmacologically active agent, over a sufficiently brief time interval, wherein the response of the biological organism to the pharmacologically active agent does not return to baseline between doses;
    b) collecting biological imaging data comprising the biological organism's response to the plurality of doses of the pharmacologically active agent administered in a), in a single imaging session, over the sufficiently brief time interval; and
    c) fitting predetermined pharmacokinetic-pharmacodynamic models to said imaging data to determine the quantitative pharmacodynamic parameters for said pharmacologically active agent comprising:
        i) setting up fit parameters and choosing a fit method;
        ii) computing best-fit parameters and their goodness of fit to the biological data using the selected fit method;
        iii) computing the statistical significance of the best-fit parameters; and
        iv) generating an output.

2. The method of claim 1 wherein the imaging data is collected on a magnetic resonance imaging device.

3. The method of claim 1, wherein the imaging data is collected on a magnetic resonance imaging device sensitive to a blood oxygen level dependent signal.

4. The method of claim 1 wherein the imaging data is collected using Positron Emission Tomography.

5. The method of claim 1 wherein the imaging data is collected on a Single Photon Emission Computed Tomography imaging device.

6. The method of claim 1 wherein the pharmacologically active agent is a medicament and the organism is a human.

7. The method of claim 1 wherein the quantitative pharmacodynamic parameters are selected from the group consisting of $E_{max}$, Hill coefficient, $EC_K$, $ED_{50}$, $k_{e0}$, and $t_{1/2eq}$.

8. The method of claim 1 wherein the imaging method does not provide stable quantitative measures.

9. The method of claim 8 wherein the non-stable quantitative measurements are used without modification in fitting predetermined pharmacokinetic pharmacodynamic models.

10. A method for quantitatively characterizing an organ's response to a pharmaceutically active agent, comprising:
    a) administering to a biological organism a plurality of doses of a pharmacologically active agent, over a sufficiently brief time interval, wherein the response of the biological organism to the pharmacologically active agent does not return to baseline between doses,
    b) collecting non-stable quantitative biological imaging data comprising a response of the organ to the plurality of doses of the pharmacologically active agent administered in a), in a single imaging session, over the sufficiently brief time interval and,
    determining quantitative pharmacodynamics parameters for the pharmacologically active agent by fitting predetermined pharmacokinetic-pharmacodynamic models to the nonquantitative biological imaging data comprising:
        i) setting up fit parameters and choosing a fit method;
        ii) computing best-fit parameters and their goodness of fit to the biological data using the selected fit method;
        iii) computing the statistical significance of the best-fit parameters; and
        iv) generating an output.

11. The method of claim 10 wherein the imaging data is collected on a magnetic resonance imaging device.

12. The method of claim 6 wherein the imaging data is collected on a magnetic resonance imaging device sensitive to blood oxygen level dependent signal.

13. The method of claim 6 wherein the imaging data is collected using Positron Emission Tomography.

14. The method of claim 6 wherein the imaging data is collected on a Single Photon Emission Computed Tomography imaging device.

15. The method of claim 6 wherein the pharmacologically active agent is a medicament and the organism is a human.

16. The method of claim 6 wherein the quantitative pharmacodynamic parameters are selected from the group consisting of $E_{max}$, Hill coefficient, $EC_{50}$, $ED_{50}$, $k_{e0}$, and $t_{1/2eq}$.

17. The method of claim 6 wherein the non-stable quantitative measurements are used without modification in fitting predetermined pharmacokinetic pharmacodynamic models.

* * * * *